United States Patent [19]
Denny et al.

[11] Patent Number: 6,124,310
[45] Date of Patent: Sep. 26, 2000

[54] ENEDIYNE COMPOUNDS

[75] Inventors: William Alexander Denny; Michael Patrick Hay; William Robert Wilson, all of Auckland, New Zealand

[73] Assignee: Mewburn Ellis, London

[21] Appl. No.: 09/011,644

[22] PCT Filed: Aug. 19, 1996

[86] PCT No.: PCT/NZ96/00084

§ 371 Date: Apr. 17, 1998

§ 102(e) Date: Apr. 17, 1998

[87] PCT Pub. No.: WO97/07118

PCT Pub. Date: Feb. 27, 1997

[30] Foreign Application Priority Data

Aug. 18, 1995 [GB] United Kingdom .................. 9517001

[51] Int. Cl.$^7$ ...................... C07G 491/08; A61K 31/435
[52] U.S. Cl. .................. 514/281; 546/44; 546/45
[58] Field of Search ................ 546/44, 45; 514/281

[56] References Cited

FOREIGN PATENT DOCUMENTS

| 415 731 | 3/1991 | European Pat. Off. . |
|---|---|---|
| 88/07378 | 10/1988 | WIPO . |
| 93/08288 | 4/1993 | WIPO . |
| 93/11099 | 6/1993 | WIPO . |
| 93/23046 | 11/1993 | WIPO . |
| 94/02450 | 2/1994 | WIPO . |
| 95/12678 | 5/1995 | WIPO . |
| 97/07118 | 2/1997 | WIPO . |

OTHER PUBLICATIONS

Culver, et al., "In Vivo Gene Transfer With Retroviral Vector–Producer Cells For Treatment Of Experimental Brains Tumors," *Science* (1992) Vol. 256:1550–1552.

Englehardt, et al., "Direct Gene transfer Of Human CFTR Into Human Bronchial Epithelia Of Xenografts With E1–Deleted Adenviruses," *Nature Genetics* (1993) Vol. 4:27–34.

Huber, et al., "Retroviral–Mediated Gene Therapy For The Treatment Of Hepatocellular Carcinoma: An Innovative Approach For Cancer Therapy, " *Proc. Nat'l. Acad. Sci., USA* 91991) Vol. 88:8093–8043.

Knox, et al., "Bioactivation Of CB 1954: Reaction Of The Active 4–Hydroxylamino Derivative With Thioesters To Form The Ultimate DNA–DNA Interstrand Crosslinking Species, " *Biochemical Pharmacology* (1991) Vol. 42:1691–1697.

Knox, et al., The Bioactive Of 5–(AZIRIDIN–1–YL)–2,4–DINITROBENZAMIDE (CB1954)–II, A Comparison Of An *Escherichia Coli* Nitroeductase And Walker DT Diaphorase, *Biochemical Pharmacology* (1992) Vol. 44: 2297–2301.

Mauger, et al., "Self–Immolative Prodrugs: Candidates For Antibody–Directed Enzyme Prodrug therapy In Conjunction With A Nitroductase Enzyme, " *J. Med. Chem.* (1994) Vol. 37:3452–3458.

Ram, et al., "In Situ Retroviral–Mediated Gene Transfer For The Treatment Of Brain Tumors In Rats, " *Cancer Research* (1993) Vol. 53:83–88.

*Primary Examiner*—Alan L. Rotman
*Attorney, Agent, or Firm*—Bozicevic, Field & Francis; Pamela Sherwood

[57] ABSTRACT

The present invention provides compounds of formulae (I) and (II), where X in formula (I) represents a group cleavable by a nitroreductase or carboxypeptidase enzyme. Enzymatic activation of the compounds provide pharmaceutical compounds which may be used for the treatment of neoplastic disease.

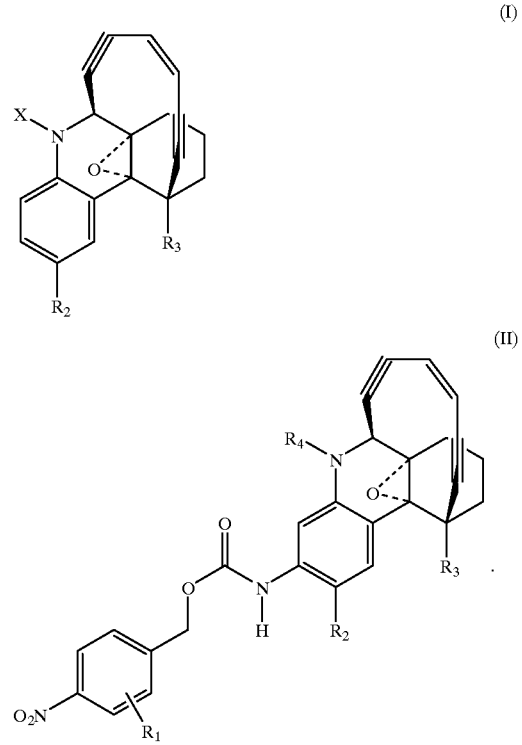

24 Claims, No Drawings

ENEDIYNE COMPOUNDS

The present invention relates to a novel class of enediyne compounds, to methods for preparing these compounds, and to their use in the treatment of neoplastic disease. In particular, the invention relates to novel nitrophenylcarbamate-based prodrugs of enediynes, suitable for use as prodrugs for GDEPT (gene-directed enzyme-prodrug therapy).

BACKGROUND TO THE INVENTION

The use of prodrugs represents a clinically very valuable concept in cancer therapy since, particularly where the prodrug is to be converted to an anti-tumour agent under the influence of an enzyme that is linkable to a monoclonal antibody that will bind to a tumour associated antigen, the combination of such a prodrug with such an enzyme monoclonal/antibody conjugate represents a very powerful clinical agent. This approach to cancer therapy, often referred to as "antibody directed enzyme/prodrug therapy" (ADEPT) is disclosed in WO88/07378.

A further therapeutic approach termed "virus-directed enzyme prodrug therapy" (VDEPT) has been proposed as a method for treating tumour cells in patients using prodrugs. Tumour cells are targeted with a viral vector carrying a gene encoding an enzyme capable of activating a prodrug. The gene may be transcriptionally regulated by tissue specific promoter or enhancer sequences. The viral vector enters tumour cells and expresses the enzyme, in order that a prodrug is converted to an active drug within the tumour cells (Huber et al, Proc. Natl. Acad. Sci. USA (1991) 88, 8039). Alternatively, non-viral methods for the delivery of genes have been used. Such methods include calcium phosphate co-precipitation, microinjection, liposomes, direct DNA uptake, and receptor-mediated DNA transfer. These are reviewed in Morgan & French, Annu. Rev. Biochem., 1993,62; 191. The term "GDEPT" (gene-directed enzyme prodrug therapy) is used to include both viral and non-viral delivery systems.

Naturally-occurring enediyne antibiotics, including dynemicin Konishi, M. et al, *J. Chem. Soc.* 1990, 112, 3715–3716, esperamicin (Golik, J. et al, *J. Amer. Chem. Soc.* 1987, 109, 3462–3464) and calicheamicin (Lee, M. D. et al, *J. Amer. Chem. Soc.* 1987, 109, 3464–3466) are very potent cytotoxins, with $IC_{50}$ values for inhibition of growth of tumour cell cultures in the low pM range. This extreme potency makes them attractive as potential effectors for prodrugs (Maier, M. E. *Synlett.* 1995, 13–26). The cytotoxic effects of these compounds are triggered by molecular rearrangements which bring the conjugated triple bonds of the enediyne core sufficiently close to initiate an electrocyclic reaction (Bergman, R. G. *Acc. Chem. Res.* 1973, 6, 25–31). Formation of a transient benzene 1,4-diradical capable of simultaneously abstracting a proton (at C-4' or C5') from a ribose moiety on each DNA chain results in a cascade of radical reactions leading to generation of double strand breaks (De Voss, J. J. et al, *J. Amer. Chem. Soc.* 1990, 112, 9669–9670).

While the natural antibiotics are very complex molecules, recent work (Nicolaou, K. C. et al, *Science* 1992, 256, 1172–1178; Nicolaou, K. C. et al, *Proc. Natl. Acad. Sci USA.* 1993, 90, 5881–5888) has described a series of simpler and more accessible synthetic analogues that are also very potent cytotoxins. A variety of releasing systems, including base-catalysed β-elimination and and photolytically generated systems have been reported (Nicolaou, K. C., et al *J. Amer. Chem. Soc.* 1992, 114, 8890–8907: Nicolaou, K. C., et al, *J. Amer. Chem. Soc.* 1993, 115, 7944–7953: Nicolaou, K. C.; Dai, W.-M. *J. Amer. Chem. Soc.* 1992, 114, 8908–8921: Wender, P. A. et al, *J. Org. Chem.* 1993, 58, 5867–5869: Wender P. A. et al, *Synthesis*, 1994, 1279–1282).

4-Nitrobenzyloxycarbonyl derivatives of a variety of classes of cytotoxins have been tested for their ability to be substrates for the aerobic nitroreductase enzyme isolated from *E. coli*. Following reduction of the nitro group of the 4-nitrobenzyloxycarbonyl group by nitroreductase enzymes, the group is destabilised and released from the cytotoxin. 4-Nitrobenzyloxycarbonyl compounds proposed in the art include derivatives of phenylenediamine mustard, actinomycin D, mitomycin C, and doxorubicin. The degree of activation of these compounds by the enzyme varies widely and unpredictably (Anlezark, G. M. et al, *J. Biochem. Pharmacol.* 1992, 44, 2289–2295: Knox, R. J. et al, *Cancer Metastasis Rev.* 1993, 12, 195–212: Knox, R. J. et al, *Biochem. Pharmacol.* 1992, 44, 2297–2301: Mauger, A. B. et al, *J. Med. Chem.* 1994, 37, 3452–3458).

We have now found that 4-nitrobenzylcarbamate derivatives of enediynes are unexpectedly good substrates for nitroreductase, and are thus of potential use as prodrugs for GDEPT in conjunction with this enzyme.

SUMMARY OF THE INVENTION

In one aspect, the invention provides compounds of general formula (I):

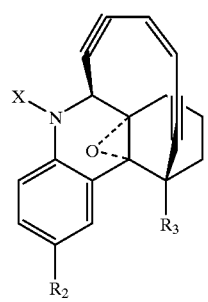

(I)

in which X is a group of the formula (Ia) or (Ib)

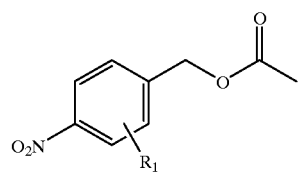

(Ia)

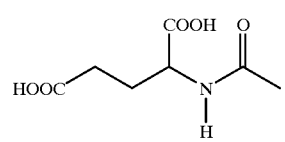

(Ib)

wherein $R_1$ represents H, R, NRR, CONHR, OR, $NHCO_2R$, $CO_2R$, $SO_2R$, $NO_2$ or up to four F atoms, $R_2$ represents H, OH, OR or $O(CH_2)_nX(CH_2)_mR$, $R_3$ represents H, OH or OR, where n is from 1 to 5, m is from 1 to 5, X is O, NH, OCO, OCONH, CONH, NHCO or NHCOO and R is lower alkyl (up to six carbon atoms) optionally substituted with from 1 to 4 groups which may be the same or different selected from hydroxyl, methoxy, amino, dimethylamino or carboxylic acid groups, or a moiety of formula (Ic)

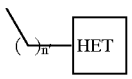

(Ic)

where n' is from 1 to 6 and HET represents a five or six membered hetrocycle containing up to 2 atoms selected from O, S and N; or a physiologically functional derivative thereof.

In a second aspect, the invention provides compounds of general formula (II):

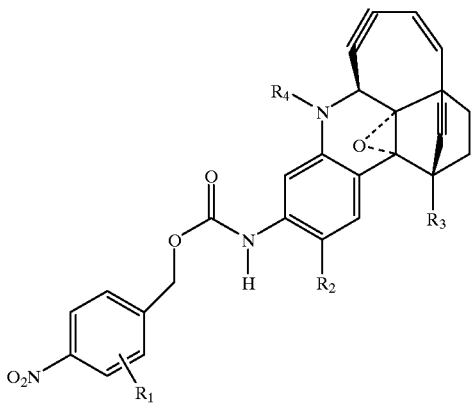

(II)

wherein $R_1$, $R_2$ and $R_3$ are as defined above, and $R_4$ represents H, benzyloxycarbon allyoxycarbonyl or $C_{1-6}$ alkoxycarbonyl (eg. ethoxycarbonyl) or a phenoxycarbonyl group optionally substituted with up to 2 groups, which may be the same or different, selected from nitro and R where R is as defmed above, or a physiologically functional derivative thereof.

It is recognised that compounds of formulae (I) and (II) may exist in one of two different enantiomeric forms. In such cases it is to be understood that formulae (I) and (II) represent either enantiomeric form or a mixture of both.

We have found that compounds of formulae (I) (in which X is a group (Ia)) and (II) are relatively non-toxic prodrugs capable of being activated by the aerobic nitroreductase from E. coli. Compounds of the formula (I) in which X is a group (Ib) are capable of being activated by a carboxypeptidase enzyme.

In another aspect, the present invention relates to the use of the compounds of formulae (I) and (II) as anticancer drugs. The compounds may be used for the selective killing of oxic and hypoxic tumour cells in methods of treatment of cancers for example leukaemias, and particularly solid cancers including breast, bowel and lung tumours, including small cell lung carcinoma.

In a further aspect, the present invention relates to the use of the compounds of formula (I) or (II), in conjunction the enzyme nitroreductase (for example isolated from E. coli) in methods of ADEPT or GDEPT therapy.

The invention also provides pharmaceutical compositions comprising a compound of the formula (I) or the formula (II) together with a pharmaceutically acceptable carrier or diluent.

DETAILED DESCRIPTION OF THE INVENTION

A. Synthesis of Compounds of the Formula (I)

The compounds of formula (I) in which X is a group (Ia) may be prepared by reacting the known (Nicolaou, K. C. et al, *J. Amer. Chem. Soc.* 1991, 113, 3106–3114) intermediate of formula A:

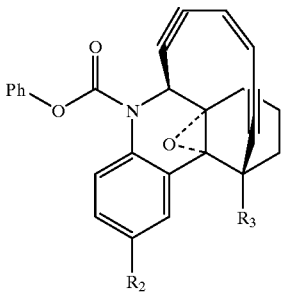

(A)

where Ph is phenyl and $R^2$ and $R^3$ are H, with an appropriately-substituted 4-nitrobenzyl alcohol and NaH under appropriate conditions, or alternatively reaction of A with an appropriately substituted 4-nitrobenzyl alcohol, 18-crown-6 and cesium carbonate under appropriate conditions.

Reference may also be made to WO 93/23046 for further details on the synthesis of starting materials of formula (A).

Compounds of the formula (I) in which X is a group (Ib) may be made by reacting compounds of the formula (I) in which X is hydrogen or phenoxycarbonyl with suitably protected glutamic acid derivatives, e.g. glutamic acid isocyanates, or glutamic acid di-tert-butyl ester in the presence of 18-crown-6 and cesium carbonate. Reference may also be made to WO88/07378 and WO91/03460 for appropriate reaction conditions.

B. Synthesis of Compounds of the Formula (II)

These compounds may be made by reference to Scheme 1 attached and in accordance with the following scheme:

Reaction of 3-amino-7,8,9,10-tetrahydrophenanthridine (1) with 2-nitrobenzylchloroformate and triethylamine in DCM gives the carbamate (2). Reaction of (2) with MCPBA in DCM gives the N-oxide (3) which can be treated with acetic anhydride for 4 hours at room temperature to give the acetate (4). Stirring a solution of the acetate (4) in MeOH with Amberlite resin IRA-400 for 16 hours gives the alcohol (5) which can be treated with t-butyldimethylsilyl triflate in DCM in the presence of triethylamine to give the silyl-protected phenanthridine (6). Compound (6) can be deprotected by photolysis to give aniline (7), which can be alkylated with trityl chloride and triethylamine in DCM to give (8). Reaction of (8) with a solution of ethynyl magnesium bromide in THF at –78° C. followed by phenyl chloroformate gives compound (9). Removal of the trityl group with trifluoroacetic acid gives (10), which can be treated with 4-nitrobenzyl chloroformate and triethylamine to give (11). Reaction of (11) with MCPBA in DCM gives the epoxide (12), which can be deprotected with TBAF to give the alcohol (13). Oxidation of 13 with PCC and 4A molecular sieves in DCM gives ketone (14). Reaction of 14 with chloride (15) in the presence of $Pd(PPh_3)_4$, CuI and $nBuNH_2$ gives enediyne (16), which can be deprotected with silver nitrate followed by KCN to give (17). Treatment of 17 with LDA in toluene then gives the required enediyne (18).

C. GDEPT.

C(i)—Vector Systems.

In general, the vector for use in GDEPT therapies may be any suitable DNA or RNA vector.

Suitable viral vectors include those which are based upon a retrovirus. Such vectors are widely available in the art.

Huber et al (ibid) report the use of amphotropic retroviruses for the transformation of hepatoma, breast, colon or skin cells. Culver et al (Science (1992) 256; 1550–1552) also describe the use of retroviral vectors in GDEPT. Such vectors or vectors derived from them may also be used. Other retroviruses may also be used to make vectors suitable for use in the present invention. Such retroviruses include rous sarcoma virus (RSV).

Englehardt et al (Nature Genetics (1993) 4; 27–34) describe the use of adenovirus based vectors in the delivery of the cystic fibrosis transmembrane conductance product (CFTR) into cells, and such adenovirus based vectors may also be used. Vectors utilising adenovirus promoter and other control sequences may be of use in delivering a system according to the invention to cells in the lung, and hence useful in treating lung tumours.

Other vector systems including vectors based on the Molony murine leukaemia virus are known (Ram, Z et al, Cancer Research (1993) 53;83–88; Dalton & Treisman, Cell (1992) 68; 597–612). These vectors contain the Murine Leukaemia virus (MLV) enhancer cloned upstream at a β-globin minimal promoter. The β-globin 5' untranslated region up to the initiation ATG is supplied to direct efficient translation of the enzyme.

Suitable promoters which may be used in vectors described above, include MLV, CMV, RSV and adenovirus promoters. Preferred adenovirus promoters are the adenovirus early gene promoters. Strong mammalian promoters may also be suitable. An example of such a promoter is the EF-1α promoter which may be obtained by reference to Mizushima and Nagata ((1990), Nucl. Acids Res. 18; 5322). Variants of such promoters retaining substantially similar transcriptional activities may also be used.

C(ii)—Nitroreductase.

Preferably, the nitroreductase enzyme is a non-mammalian nitroreductase enzyme, such as a bacterial nitroreductase. An *E.coli* nitroreductase as disclosed in WO93/08288 is particularly preferred. The enzyme may be modified by standard recombinant DNA techniques, e.g. by cloning the enzyme, determining its gene sequence and altering the gene sequence by methods such as truncation, substitution, deletion or insertion of sequences for example by site-directed mutagenesis. Reference may be made to "Molecular Cloning" by Sambrook et al (1989, Cold Spring Harbor) for discussion of standard recombinant DNA techniques. The modification made may be any which still leaves the enzyme with the ability to reduce the nitro group of the protecting 4-nitrobenzyl group but alters other properties of the enzyme, for example its rate of reaction or selectivity.

In addition, small truncations in the N- and/or C-terminal sequence may occur as a result of the manipulations required to produce a vector in which a nucleic acid sequence encoding the enzyme is linked to the various other vector sequences.

C(iii) Carboxypeptidase

The enzyme is preferably a bacterial carboxypeptidase, especially carboxypeptidase CPG2 or Pseudomonas γ-glutamylhydrolase EC3.4.22.12 (Levy C C & Goldman P J. Biol. Chem. 242; p2933 (1967).

Carboxypeptidase G2 (CPG2) is disclosed in WO88/07378. Although native CPG2 is preferred, alterations to its sequence which are amino acid substitutions, deletions or insertions (eg. of about 1, 2, 3, 4, 5, 10 or 20 residues in each case) are also possible. In any event, the alteration will be such that the enzyme retains its ability to convert a prodrug to an active drug at substantially the same rate as the native enzyme. In this context, "substantially the same rate" will desirably be within 1 order of magnitude, and preferably from about 50-fold e.g. about 2-fold less to 2, 5 or 10 fold more.

In addition to specific changes the enzyme may otherwise be altered by truncation, substitution, deletion or insertion as long as the activity of the enzyme is substantially unchanged as defined above. For example, small truncations in the N- and/or C-terminal sequence may occur as a result of the manipulations required to produce a vector in which a nucleic acid sequence encoding the enzyme is linked to a suitable promoter.

D. ADEPT.

For applications in ADEPT systems, an antibody directed against a tumour specific marker is linked to the nitroreductase or carboxypeptidase enzyme, which may be modified as described above. The antibody may be monoclonal or polyclonal. For the purposes of the present invention, the term "antibody", unless specified to the contrary, includes fragments of whole antibodies which retain their binding activity for a tumour target antigen. Such fragments include Fv, F(ab') and F(ab')$_2$ fragments, as well as single chain antibodies. Furthermore, the antibodies and fragments thereof may be humanised antibodies, eg. as described in EP-A-239400.

The antibodies may be produced by conventional hybridoma techniques or, in the case of modified antibodies or fragments, by recombinant DNA technology, eg by the expression in a suitable host vector of a DNA construct encoding the modified antibody or fragment operably linked to a promoter. Suitable host cells include bacterial (eg. *E.coli*), yeast, insect and mammalian. When the antibody is produced by such recombinant techniques the enzyme may be produced by linking a nucleic acid sequence encoding the enzyme (optionally modified as described above) to the 3' or 5' end of the sequence of the construct encoding the antibody or fragment thereof.

E. Physiologically Functional Derivatives.

Physiologically functional derivatives of prodrugs include salts, amides and esters. Esters include carboxylic acid esters in which the non-carbonyl moiety of the ester grouping is selected from straight or branched chain $C_{1-6}$alkyl, (methyl, n-propyl, n-butyl or t-butyl); or $C_{3-6}$cyclic alkyl (e.g. cyclohexyl). Salts include physiologically acceptable base salts, eg derived from an appropriate base, such as alkali metal (e.g. sodium), alkaline earth metal (e.g. magnesium) salts, ammonium and $NR_4$. (wherein R" is $C_{1-4}$ alkyl) salts. Other salts include acid addition salts, including the hydrochloride and acetate salts. Amides include non-substituted and mono- and di-substituted derivatives. Such derivatives may be prepared by techniques known per se in the art of pharmacy.

F. Applications of the Invention.

The compounds of the invention can be used in a method of treatment of the human or animal body. Such treatment includes a method of treating the growth of neoplastic cells in a patient with neoplastic disease which comprises administering to a patient in need of treatment compounds of the invention as part of an ADEPT or GDEPT therapy system. Neoplastic diseases include leukaemia and solid tumours such as breast, bowel and lung tumours including small cell lung carcinoma.

It will be understood that where treatment of tumours is concerned, treatment includes any measure taken by the physician to alleviate the effect of the tumour on a patient. Thus, although complete remission of the tumour is a desirable goal, effective treatment will also include any measures capable of achieving partial remission of the tumour as well as a slowing down in the rate of growth of a tumour including metastases. Such measures can be effective in prolonging and/or enhancing the quality of life and relieving the symptoms of the disease.

F(i): ADEPT Therapy.

The antibody/enzyme conjugate for ADEPT can be administered simultaneously but it is often found preferable, in clinical practice, to administer the enzyme/agent conjugate before the prodrug, e.g. up to 72 hours or even 1 week before, in order to give the enzyme/agent conjugate an opportunity to localise in the region of the tumour target. By operating in this way, when the prodrug is administered, conversion of the prodrug to the cytotoxic agent tends to be confined to the regions where the enzyme/agent conjugate is localised, i.e. the region of the target tumour the premature release of the compound of formula (II) is minimised.

In ADEPT the degree of localisation of the enzyme/agent conjugate (in terms of the ratio of localized to freely circulating active conjugate) can be further enhanced using the clearance and/or inactivation systems described in WO89/10140. This involves, usually following administration of the conjugate and before administration of the prodrug, the administration of a component (a "second component") which is able to bind to the such part of the conjugate so as to inactivate the enzyme and/or accelerate the clearance of the conjugate from the blood. Such a component may include an antibody to the enzyme component of the system which is capable of inactivating the enzyme.

The second component may be linked to a macromolecule such as dextran, a liposome, albumin, macroglobulin or a blood group O erythrocyte so that the second component is restrained from leaving the vascular compartment. In addition or as an alternative, the second component may include a sufficient number of covalently bound galactose residues, or residues of other sugars such as lactose or mannose, so that it can bind the conjugate in plasma but be removed together with the conjugate from plasma by receptors for galactose or other sugars in the liver. The second component should be administered and designed for use such that it will not, to any appreciable extent, enter the extravascular space of the tumour where it could inactivate localised conjugate prior to and during administration of the prodrug.

In ADEPT systems, the dose of the prodrug and conjugate will ultimately be at the discretion of the physician, who will take into account such factors as the age, weight and condition of the patient. Suitable doses of prodrug and conjugate are given in Bagshawe et al. Antibody, Immunoconjugates, and Radiopharmaceuticals (1991), 4, 915–922. A suitable dose of conjugate may be from 500 to 200,000 enzyme units/m$^2$ (e.g. 20,000 enzyme units/m$^2$) and a suitable dose of prodrug may be from about 0.1 to 200 mg/Kg, preferably about from 10 to 100 mg/Kg per patient per day.

In order to secure maximum concentration of the conjugate at the site of desired treatment, it is normally desirable to space apart administration of the two components by at least 4 hours. The exact regime will be influenced by various factors including the nature of the tumour to be targeted and the nature of the prodrug, but usually there will be an adequate concentration of the conjugate at the site of desired treatment within 48 hours.

The ADEPT system when used with nitroreductase also preferably comprises a suitable cofactor for the enzyme. Suitable cofactors include a riboside or ribotide of nicotinic acid or nicotinamide.

The antibody/enzyme conjugate may be administered by any suitable route usually used in ADEPT therapy. This includes parenteral administration of the antibody in a manner and in formulations similar to that described in section F(iv) below.

F(ii): GDEPT Therapy.

For use of the vectors in therapy, the vectors will usually be packaged into viral particles and the particles delivered to the site of the tumour, as described in for example Ram et al (ibid). The viral particles may be modified to include an antibody, fragment thereof (including a single chain) or tumour-directed ligand to enhance targeting of the tumour. Alternatively the vectors may be packaged into liposomes. The liposomes may be targeted to a particular tumour. This can be achieved by attaching a tumour-directed antibody to the liposome. Viral particles may also be incorporated into liposomes. The particles may be delivered to the tumour by any suitable means at the disposal of the physician. Preferably, the viral particles will be capable of selectively infecting the tumour cells. By "selectively infecting" it is meant that the viral particles will primarily infect tumour cells and that the proportion of non-tumour cells infected is such that the damage to non-tumour cells by administration of a prodrug will be acceptably low, given the nature of the disease being treated. Ultimately, this will be determined by the physician.

One suitable route of administration is by injection of the particles in a sterile solution. Viruses, for example isolated from packaging cell lines may also be administered by regional perfusion or direct intratumoral direction, or direct injection into a body cavity (intracaviterial administration), for example by intra-peritoneum injection.

The exact dosage regime for GDEPT will, of course, need to be determined by individual clinicians for individual patients and this, in turn, will be controlled by the exact nature of the prodrug and the cytotoxic agent to be released from the prodrug but some general guidance can be given. Chemotherapy of this type will normally involve parenteral administration of modified virus and administration by the intravenous route is frequently found to be the most practical.

In GDEPT systems the amount of virus or other vector delivered will be such as to provide a similar cellular concentration of enzyme as in the ADEPT system mentioned above. Typically, the vector will be administered to the patient and then the uptake of the vector by transfected or infected (in the case of viral vectors) cells monitored, for example by recovery and analysis of a biopsy sample of targeted tissue. This may be determined by clinical trials which involve administering a range of trial doses to a patient and measuring the degree of infection or transfection of a target cell or tumour. The amount of prodrug required will be similar to or greater than that for ADEPT systems.

In using a GDEPT system the prodrug will usually be administered following administration of the vector encoding an enzyme. Suitable doses of prodrug are from about 0.1 to 200 mg/Kg, preferably about from 10 to 100 mg/Kg per patient per day.

F(iv): Administration of Drug or Prodrug,

While it is possible for the compounds of the invention to be administered alone it is preferable to present them as pharmaceutical formulations. The formulations comprise the compounds, together with one or more acceptable carriers thereof and optionally other therapeutic ingredients. The carrier or carriers must be "acceptable" in the sense of being compatible with the other ingredients of the formulation and not deleterious to the recipients thereof, for example, liposomes. Suitable liposomes include, for example, those comprising the positively charged lipid (N[1-(2,3-dioleyloxy)

propyl]-N,N,N-triethylammonium (DOTMA), those comprising dioleoylphosphatidylethanolamine (DOPE), and those comprising 3β[N-(n',N'-imethylaminoethane)-carbamoyl]cholesterol (DC-Chol).

Formulations suitable for parenteral or intramuscular administration include aqueous and non-aqueous sterile injection solutions which may contain anti-oxidants, buffers, bacteriostats, bactericidal antibiotics and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose containers, for example sealed ampoules and vials, and may be stored in a freeze-dried (lyophilized) condition requiring only the addition of the sterile liquid carrier, for example water, for injections, immediately prior to use. Injection solutions and suspensions may be prepared extemporaneously from sterile powders, granules and tablets of the kind previously described.

It should be understood that in addition to the ingredients particularly mentioned above the formulations may include other agents conventional in the art having regard to the type of formulation in question. Of the possible formulations, sterile pyrogen-free aqueous and non-aqueous solutions are preferred.

The doses may be administered sequentially, eg. at daily, weekly or monthly intervals, or in response to a specific need of the patient. Preferred routes of administration are oral delivery and injection, typically parenteral or intramuscular injection or intratumoural injection.

The exact dosage regime will, of course, need to be determined by individual clinicians for individual patients and this, in turn, will be controlled by the exact nature of compound but some general guidance can be given. Typical dosage ranges generally will be those described above which may be administered in single or multiple doses. Other doses may be used according to the condition of the patient and other factors at the discretion of the physician.

The following Examples illustrate the invention.

EXAMPLE 1

A solution of the known (Nicolaou, K. C.; Smith, A. L.; Wendeborn, S. V.; Hwang, C.-K. J. Amer. Chem. Soc. 1991, 113, 3106–3114) enediyne of formula A':

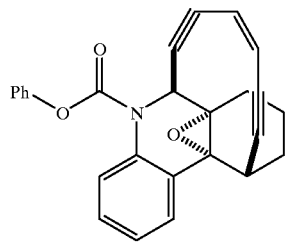

(A')

(0.188 mg, 0.47 mmol) in THF (2 mL) was added to a stirred solution of 4-nitrobenzyl alcohol (22.0 mg, 1.43 mmol) and NaH (50% dispersion, 69 mg, 1.43 mmol) in THF at 0° C. under N2. The solution was stirred at 0° C. for 10 min and sat NH4Cl solution (5 ml) added. The mixture was extracted with EtOAc (3×20 mL), the combined organic fraction washed with brine (30 mL), dried (Na2SO4) and the solvent removed under reduced pressure. The residue was chromatographed, eluting with 40% diethyl ether/pet. ether, to give (6R,6aR,10R,10aS,14Z)-(±)-(4-nitrophenyl)methyl 7,8,9,10-tetrahydro-6a,10a-epoxy-6, [3]-hexene[1,5] diynophenanthridine-5(6H)-carboxylate (67 mg, 31%) mp (gum) 59–63° C.; (KBr) 2955, 2933, 2863, 1709, 1524, 1495, 1389, 1271 cm-1; 1H NMR ((CD3)2SO) d 8.21 (d, J=8.8 Hz, 2 H, H 3'''), 7.69 (dd, J=7.9, 1.3 Hz, 1 H, H 1), 7.58 (d, J=8.5 Hz, 2 H, H 2'''), 7.38 (dd, J=8.1, 1.2 Hz, 1 H, H 4), 7.31 (ddd, J=8.1, 7.4, 1.4 Hz, 1 H, H 3), 7.22 (ddd, J=7.7, 7.5, 1.3 Hz, 1 H, H 2), 5.97 (dd, J=9.9, 1.6 Hz, 1 H, H 4'), 5.84 (dd, J=9.9, 1.7 Hz, 1 H, H 3'), 5.47 (d, J=1.5 Hz, 1 H, H 6), 5.35 (d, J=13.8 Hz, 1 H, H 1"), 5.30 (d, J=13.8 Hz, 1 H, H 1"), 3.99 (s, 1 H, H 10), 2.29–2.34 (m, 1 H, H 7), 2.07–2.12 (m, 1 H, H 7), 1.67–1.85 (m, 3 H, H 8, 2H 9), 1.54–1.58 (m, 1 H, H 8); 13C NMR ((CD3)2SO) d 151.0 (OCO), 147.0 (C 4'''), 143.7 (C 1'''), 135.0 (C 4a) 128.2 (C 1a), 128.0 (C 2'''), 127.9 (C 3), 127.3 (C 1), 125.9 (C 4), 125.6 (C 4'), 124.9 (C 2), 123.4 (C 3'''), 122.0 (C 3'), 102.2 (C 6'), 93.9 (C 1'), 90.9 (C 5'), 88.7 (C 2'), 69.8); (C 6a), 66.2 (C 1''), 60.4 (C 10a), 49.0 (C 6), 28.4 (C 10), 22.7 (C 7), 22.0 (C 9), 15.1 (C 8); MS (DEI) 452 (60%, M+), 316 (30), 272 (60), 244 (70), 216 (100), 136 (95); HRM (DEI) calcd for C27H20N2O5 (M+): 452.1372, found 452.1375. 1H NMR and 13C NMR assignments were determined on the basis of COSY, HMBC and HMQC experiments. Also recovered was starting material (12%).

Alternatively, the above compound can be prepared by adding 18-crown-6 (0.41 g, 0.25 mmol) and 4-nitrobenzyl alcohol (78 mg, 0.51 mmol) to a stirred solution of cesium carbonate (0.41 g, 1.27 mmol) in acetonitrile (15 mL), and stirring this for a further 10 min at 20° C. Compound A' (100 mg, 0.25 mmol) was added, and the mixture was stirred for 24 h at 20° C. The solvent was removed under reduced pressure and the residue was chromatographed on silica gel. Elution with Et₂O/petroleum ether (4:6) gave the desired 4-nitrobenzyl compound (72 mg, 68%).

EXAMPLE 2

The compound prepared in Example 1 was activated by the aerobic nitroreductase from E. coli, by being incubated with UV4 cells for 18 hours in 96-well plates under aerobic conditions. The compound 2 had an IC$_{50}$ of 18.1 μM. but when incubated under the same conditions, together with the purified E. coli nitroreductase enzyme (1 μg/mL) and NADH (1 mM, as cofactor) showed an IC$_{50}$ of 0.19 μM. This represents a 115-fold activation by the enzyme, and demonstrates the potential usefulness of the compound as a prodrug for GDEPT in conjunction with this enzyme. In contrast, neither compound of formula A' or the known (A. L. Smith et al., U.S. Pat. No. 5,276,159; Chem. Abstracts 1994, 121, 280470v) closely-related compound of formula B:

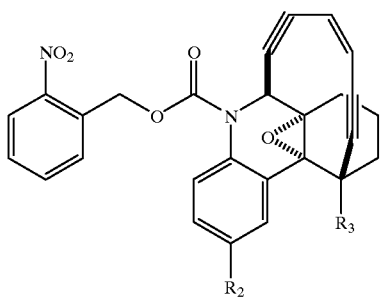

(B)

showed any activation by the enzyme.

EXAMPLE 3
Preparation of Compound 4 (Scheme 2).

A mixture of compound (1) [prepared by the method of K. C. Nicolaou, P. Maligres, T. Suzuki, S. V. Wendebom, W.-M. Dai, and R. K. Chandha, J. Am. Chem. Soc., 1992, 114, 8890–8907] (.0.57 g, 1.15 mmol), TBDMSOCH$_2$CH$_2$OSO$_2$PhMe (1.53 g, 4.62 mmol), Cs$_2$CO$_3$ (5.64 g, 17.3 mmol) and 18-rown-6 (1.53 g, 5.77 mmol) in acetonitrile (100 mL) was stirred at 20° C. for 16 h. The mixture was filtered through celite and the solvent removed under reduced pressure. The residue was suspended in diethyl ether (150 mL), filtered through celite, washed with diethyl ether (2×20 mL), and the combined organic extracts evaporated under reduced pressure. The residue was chromatographed on silica, eluting with a gradient (10–20%) of EtOAc/petroleum ether to give compound (2) as a foam (354 mg 54%). IR $\upsilon_{max}$ (thin film) 2951, 2930, 2857, 2857, 1723, 1505, 1377, 1273, 1200 cm$^{-1}$, $^1$H NMR (CDCl$_3$) d 7.32–7.36 (m, 3 H, H$_{arom}$), 7.14–7.21 (m, 4H, H$_{arom}$), 6.86 (dd, J=8.8, 2.7 Hz, 1 H, H$_{arom}$), 5.78 (dd, J=9.8, 1.3 Hz, 1 H, CH=C), 5.67 (dd, J=9.8, 1.4 Hz, 1 H, CH=C), 5.48 (s, 1 H, NCH), 4.04–4.07 (m, 2 H, CH$_2$O), 3.95–3.98 (m 2H, CH$_2$O), 3.73 (brs, 1 H, CH), 2.38–2.44 (m, 2H, CH$_2$) 2.19–2.27 (m, 1H, CH$_2$), 0.90 (s, 9H, SiC (CH$_3$)$_3$), 0.10 (s, 6H, Si(CH$_3$)$_2$). $^{13}$C NMR (CDCl$_3$) d 156.2, 154.6, 151.0, 135.5, 129.2, 128.6, 127.3, 125.5, 124.9, 121.9, 121.5, 113.9, 113.7, 101.5, 94.0, 91.3, 88.8, 69.9, 69.5, 61.9, 60.9, 50.0, 29.5, 25.8, 23.2, 22.2, 18.3, 15.6, −5.4. DEIMS m/z 567 (M$^+$, 50%), 510 (100), 266 (20), 372 (30). HRDEIMS calc. for C$_{34}$H$_{37}$NO$_5$Si (M$^+$) 567.2441, found 567.2440.

A solution of (2) (317 mg, 0.55 mol) in acetonitrile (5 mL) was added to a suspension of 4-nitrobenzyl alcohol (253 mg, 1.65 mmol), Cs$_2$CO$_3$ (1.07 g, 3.30 mmol) and 18-crown-6 (14 mg, 0.55 mmol) in acetonitrile (20 mL) and the mixture stirred at 20° C. for 16 h. The mixture was filtered through celite, washed with ether (50 mL) and the solvent removed under reduced pressure. The residue was chromatographed on silica, eluting with a gradient (30–50%) of diethyl ether/pet. ether to give (3) as an oil, 39 mg (11%) IR $\upsilon_{max}$ (thin film) 2949, 2930, 2857, 1707, 1607, 1522, 1505, 1346, 1271, 1100 cm$^{-1}$.

A solution of (3) (39 mg, 62 mmol) in THF (2 mL) was treated with TBAF (1M in THF, 70 mL, 70 mmol) and stirred at 20° C. for 30 minutes. The solvent was removed under reduced pressure and the residue chromatographed on silica, eluting with a gradient (50–80%) of diethyl ether/petroleum ether to give (4) (17 mg, 54%). IR $\upsilon_{max}$ (thin film) 3440, 2951, 2926, 2855, 1707, 1521, 1503, 1346, 1273 cm$^{-1}$; $^1$H NMR (CDCl$_3$) d 8.19 (d, J=7.6 Hz, 2H, H$_{arom}$), 7.42 (br s, 2H, H$_{arom}$), 6.86 (dd J=8.8, 2.6 Hz, 1H, H$_{arom}$), 5.79 (dd, J=9.9, 1.6 Hz, 1H, CH=), 5.76 (dd, J=9.9,1.6 Hz, 1H, CH=), 5.41 (brs, 1H, NCH), 5.29 (s, 2H, CH$_2$O), 4.10 (brt, J=4.4 Hz, 2H, CH$_2$O), 3.97 (brt, J=4.4 Hz, 2H, CH$_2$O), 3.71 (brs, 1H, CH), 2.35–2.41 (m, 1H, CH$_2$), 2.15–2.24 (m, 1H, CH$_2$), 2.15–2.24 (m, 1H, CH$_2$), 1.88–2.04, (m, 3H, CH$_2$, OH), 1.66–1.82 (m, 1H, CH$_2$), 1.57–1.62 (m, 1H, CH$_2$). $^{13}$C NMR (CDCl$_3$) d 156.0, 154.8, 147.6, 143.4, 135.7, 130.8, 130.0, 127.6, 125.0, 123.8, 121.9, 113.8, 113.7, 101.5, 93.9, 91.5, 88.9, 70.1, 69.5, 66.5, 61.4, 61.0, 50.0, 29.5, 23.2, 22.5, 15.6.

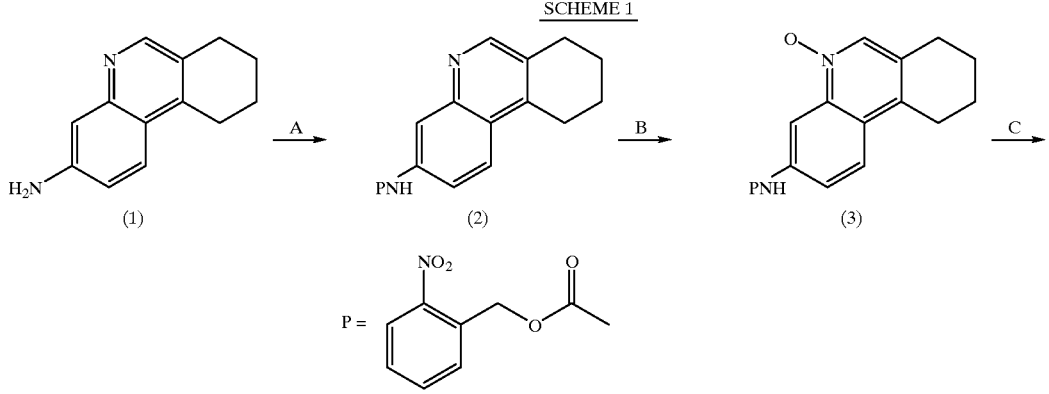

SCHEME 1

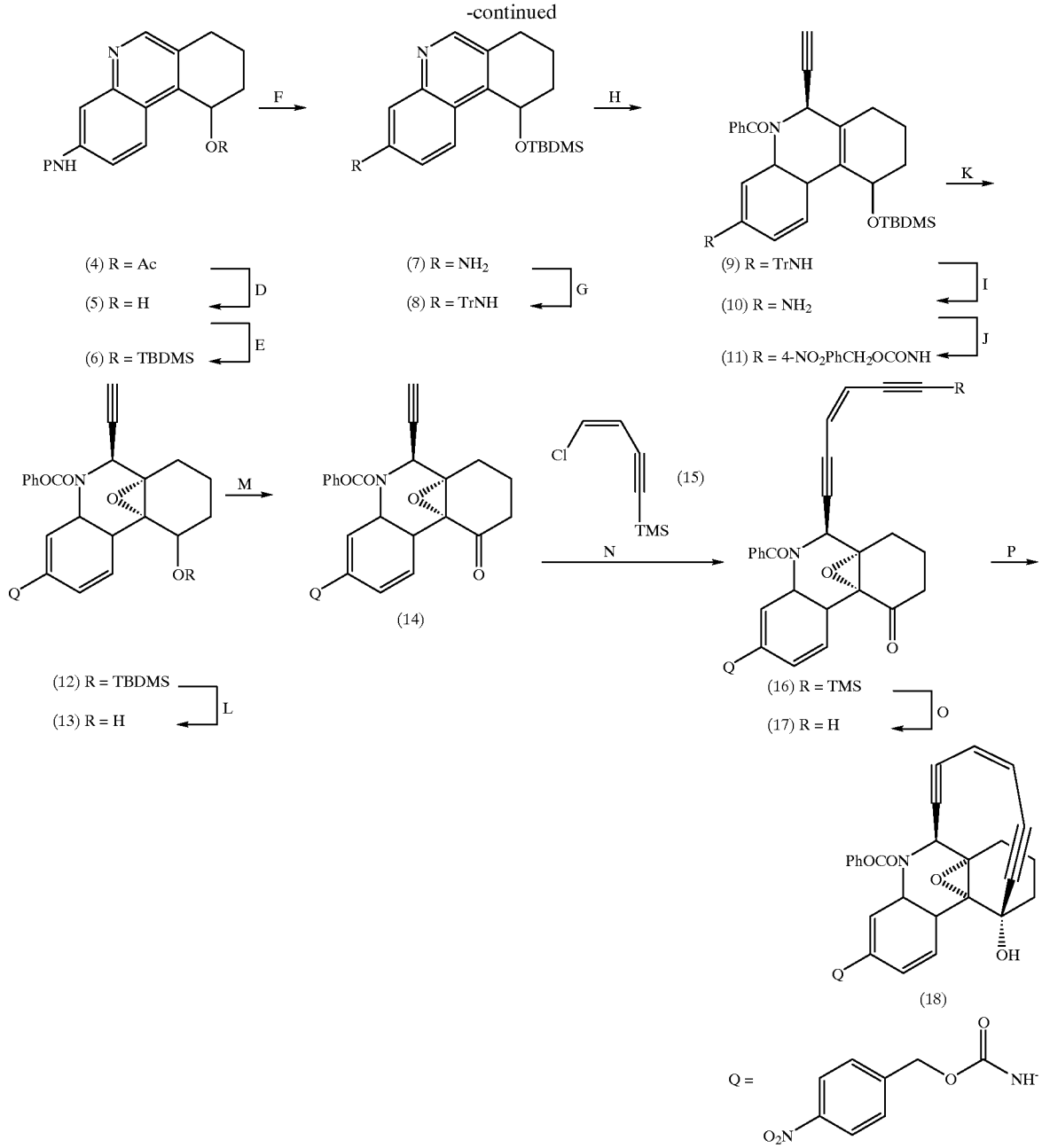

REAGENTS FOR SCHEME 1

A 2-nitrobenzyl chloroformate/Et$_3$N/CH$_2$Cl$_2$.
B MCPBA/CH$_2$Cl$_2$.
C Ac$_2$O/25° C.
D Amberlite resin IRA-144/MeOH.
E TBDMS-Tf/2,6-lutidine.
F UV light/CH$_2$Cl$_2$/25° C.
G TrCl/Et$_3$N/THF.
H ethynylMgBr, then PhOCOCl/THF/−78° C.
I TFA/MeOH/25° C.
J 4-nitrobenzyl chloroformate/Et$_3$N/CH$_2$Cl$_2$.
K MCPBA/CH$_2$Cl$_2$.
L TBAF/THF.
M PCC/4 Å molecular sieves.
N Cl—C≡C-TMS, Pd(PPh$_3$)$_4$, CuI, nBuNH$_2$/CH$_2$Cl$_2$.
O AgNO$_3$/THF/EtOH/H$_2$O, KCN.

P LDA/toluene.

Scheme 2

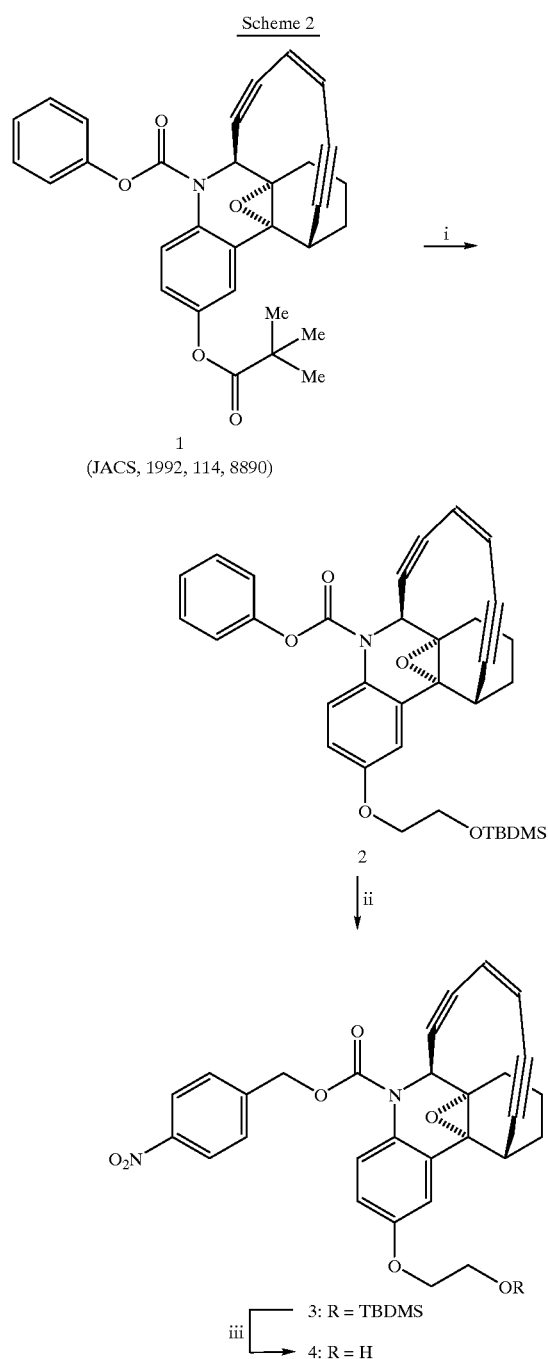

i: TBDMS(CH$_2$)$_2$OSO$_2$PhMe/18-crown-6/Cs$_2$CO$_3$/ MeCN/16 h/20° C.

ii: 4-NO$_2$PhCH$_2$OH/18-crown-6/Cs$_2$CO$_3$/16 h/20° C.

iii: TBAF/THF/30 min/20° C.

We claim:

1. A compound of formula (I):

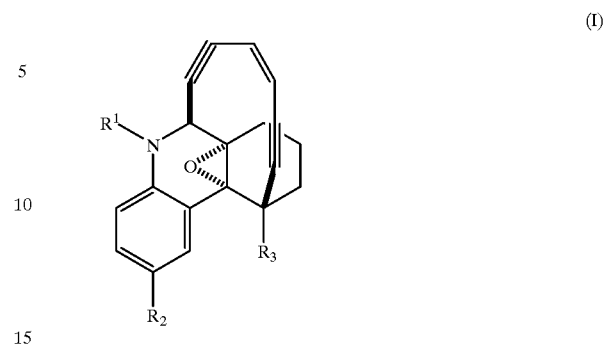

in which R$^1$ is a group of formula (Ia)

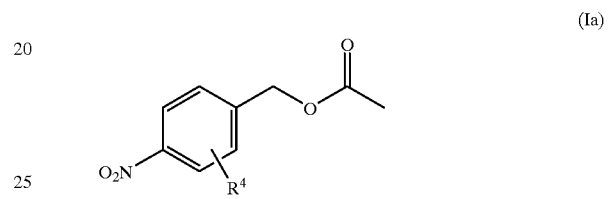

wherein R$^2$ represents H, OH, OR, R$^3$ represents H, OH or OR, where R$^4$ represents H, R, NRR, CONHR, OR, NHCO$_2$R, CO$_2$R, SO$_2$R, NO$_2$ or up to four F atoms and R is C$_{1-6}$ alkyl optionally substituted with from 1 to 4 groups which may be the same or different selected from hydroxyl, methoxy, amino, dimethylamino or carboxylic acid groups, or a moiety of formula (Ic)

where n' is from 1 to 6 and HET represents a five or six membered heterocycle having one atom selected from O, S or N; or a physiologically functional salt, amide or ester thereof.

2. A compound of formula (II):

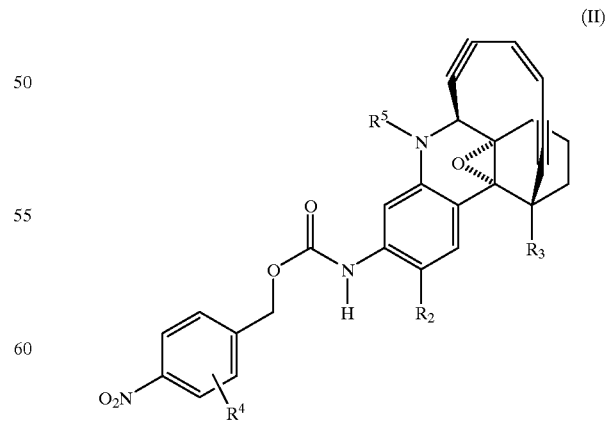

wherein $R^2$ represents H, OH, OR, $R^3$ represents H, OH or OR, where $R^4$ represents H, R, NRR, CONHR, OR, $NHCO_2R$, $CO_2R$, $SO_2R$, $NO_2$ or up to four F atoms, and $R^5$ represents H, benzyloxycarbonyl, allyoxycarbonyl or $C_{1-6}$ alkyxycarbonyl or a phenoxycarbonyl group optionally substituted with up to 2 groups, which may be the same or different, selected from nitro and R where R is $C_{1-6}$ alkyl optionally substituted with from 1 to 4 groups which may be the same or different selected from hydroxyl, methoxy, amino, dimethylamino or carboxylic acid groups, or a moiety of formula (Ic)

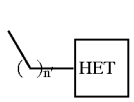
(Ic)

where n' is from 1 to 6 and HET represents a five or six membered heterocycle having one atom selected from O, S or N; or a physiologically functional salt, amide or ester thereof.

3. A compound of formula (I):

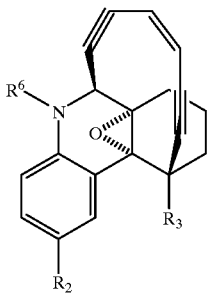

In which $R^6$ is a group of the formula (Ib)

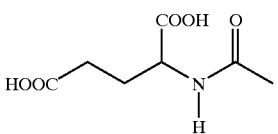

wherein $R^2$ represents H, OH, OR, $R^3$ represents H, OH or OR, where R is $C_{1-6}$ alkyl optionally substituted with from 1 to 4 groups, which may be the same or different selected from hydroxyl, methoxy, amino, dimethylamino or carboxylic acid groups or a moiety of formula (Ic)

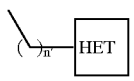
(Ic)

where n' is from 1 to 6 and HET represents a five or six membered heterocycle having one atom selected from O, S and N; or a physiologically functional salt, amide or ester thereof.

4. A composition comprising a compound according to claim 1 together with a pharmaceutically acceptable carrier or diluent.

5. A method of treating neoplastic disease, the method comprising:
administering to a patient in need of treatment sensitive to an effective amount of a compound according to claim 1.

6. A composition comprising a compound according to claim 2 together with a pharmaceutically acceptable carrier or diluent.

7. A composition comprising a compound according to claim 4 together with a pharmaceutically acceptable carrier or diluent.

8. A method according to claim 5, wherein said compound is administered together with a pharmaceutically acceptable carrier or diluent.

9. A method of treating neoplastic disease, the method comprising:
administering to a patient in need of treatment sensitive to an effective amount of a compound according to claim 2.

10. A method according to claim 9, wherein said compound is administered together with a pharmaceutically acceptable carrier or diluent.

11. A method of treating neoplastic disease, the method comprising:
administering to a patient in need of treatment sensitive to an effective amount of a compound according to claim 3.

12. A method according to claim 11, wherein said compound is administered together with a pharmaceutically acceptable carrier or diluent.

13. The compound of claim 1, wherein R is a $C_{1-6}$ alkyl optionally substituted with one to four hydroxyl or amino groups.

14. The compound of claim 2, wherein R is a $C_{1-6}$ alkyl optionally substituted with one to four hydroxyl or amino groups.

15. The compound of claim 4, wherein R is a $C_{1-6}$ alkyl optionally substituted with one to four hydroxyl or amino groups.

16. The compound of claim 1, wherein $R^2$ is H, OH or OR; $R^3$ is H, OH or OR where R is a $C_{1-6}$ alkyl optionally substituted with one hydroxy group; and $R^4$ is H.

17. The compound of claim 2, wherein $R^2$ is H, OH or OR; $R^3$ is H, OH or OR where R is a $C_{1-6}$ alkyl optionally substituted with one hydroxy group; and $R^4$ is H.

18. The compound of claim 4, wherein $R^2$ is H, OH or OR; $R^3$ is H, OH or OR where R is a $C_{1-6}$ alkyl optionally substituted with one hydroxy group; and $R^4$ is H.

19. The method of claim 8, wherein said neoplastic disease is one of leukemias and solid cancers.

20. The method of claim 19, wherein said solid cancer is one of breast, bowel or lung cancer.

21. The method of claim 9, wherein said neoplastic disease is one of leukemias and solid cancers.

22. The method of claim 21, wherein said solid cancer is one of breast, bowel or lung cancer.

23. The method of claim 11, wherein said neoplastic disease is one of leukemias and solid cancers.

24. The method of claim 23, wherein said solid cancer is one of breast, bowel or lung cancer.

* * * * *

UNITED STATES PATENT AND TRADEMARK OFFICE
CERTIFICATE OF CORRECTION

PATENT NO: 6,124,310
DATED: September 26, 2000
INVENTOR(S): William Alexander Denny, Michael Patrick Hay and William Robert Wilson It is certified that error appears in the above-identified patent and that said Letters Patent are hereby corrected as shown below:

Please delete the Assignee information in its entirety and replace with:

-- Cancer Research Campaign Technology Limited of Cambridge House, 6-10 Cambridge Terrace, Regent's Park, London NW1 4JL, United Kingdom --

Signed and Sealed this

Twenty-fourth Day of April, 2001

*Attest:*

NICHOLAS P. GODICI

*Attesting Officer*      *Acting Director of the United States Patent and Trademark Office*